United States Patent [19]
Lee-Huang et al.

[11] Patent Number: 5,484,889
[45] Date of Patent: Jan. 16, 1996

[54] PLANT PROTEIN USEFUL FOR TREATING TUMORS AND HIV INFECTION

[75] Inventors: Sylvia Lee-Huang, New York, N.Y.; Philip L. Huang, Boston, Mass.; Peter L. Nara, Frederick, Md.; Hao-Chia Chen, Potomac, Md.; Hsiang-fu Kung, Middletown, Md.; Peter Huang; Henry I. Huang, both of New York, N.Y.; Paul L. Huang, Boston, Mass.

[73] Assignees: New York University, New York, N.Y.; American Biosciences, Inc., Boston, Mass.; The United States of America as represented by the Secretary of the Department of Health and Human Services, Washington, D.C.

[21] Appl. No.: 277,283

[22] Filed: Jul. 21, 1994

Related U.S. Application Data

[63] Continuation of Ser. No. 48,066, Apr. 19, 1993, abandoned, which is a continuation of Ser. No. 594,156, Oct. 9, 1990, abandoned.

[51] Int. Cl.⁶ .................................................. C07K 14/415
[52] U.S. Cl. ................................................ 530/379; 530/370
[58] Field of Search ..................................... 530/370, 379; 435/69.1; 514/12, 21

[56] References Cited

U.S. PATENT DOCUMENTS

| | | | |
|---|---|---|---|
| 4,795,739 | 1/1989 | Lifson et al. | 514/8 |
| 4,883,761 | 11/1989 | Keith et al. | 435/320.1 |
| 5,037,960 | 8/1991 | Barbieri et al. | 530/370 |

OTHER PUBLICATIONS

Li, S.S.L. 1980. Experientia 36:524–527.
Hird et al. 1990. Gener and Cancer, (D. Carney et al; Eds.), John Wiley & Sons Ltd; N.Y. pp. 184–189.
Altman et al. 1993. "AIDS Study Cart Doubt on Value of Hastened Drug Approval in U.S.", The New York Times, Apr. 6, p. C3.
Kubota et al. 1986. Biochimica et Biophysica Acta 871:101–106.
Stirpe et al. 1986. FEBS Letters 195:1–8.

*Primary Examiner*—Keith C. Furman
*Attorney, Agent, or Firm*—Browdy and Neimark

[57] ABSTRACT

A protein, in particular MAP 30, obtainable from both the fruit and seeds of *Momordica charantia* or produced by recombinant means useful for treating tumors and HIV infections is disclosed. In treating HIV infections, the protein is administered alone or in conjunction with conventional AIDS therapies. Also provided are processes for purifying the protein, DNA sequences encoding the protein, and recombinant DNA methods for expressing the protein.

1 Claim, 6 Drawing Sheets

N-TERMINAL AMINO ACID SEQUENCE OF MAP 30 AND
ITS COMPARISON WITH TRICHOSANTHIN AND RICIN A CHAIN

```
              1                                              10
MAP 30    Asp - Val - Asn  - Phe - Asp - Leu-Ser - Thr - Ala-Thr -
Tri 1     Asp - Val - Ser  - Phe - Arg - Leu-Ser - Gly - Ala-Thr -
Ric A Pro- Ile - Ile - Asn - Phe - Thr - Thr-Ala - Gly - Ala-Thr -

11                                             20
MAP 30    Ala - Lys - Thr - Tyr - Tyr - Lys - Phe-Ile - Glu-Asp -
Tri 1     Ser - Ser - Ser - Tyr - Gly - Val - Phe-Ile - Ser-Asn -
Ric A     Val - Gln - Ser - Tyr - Thr - Asn - Phe-Ile - Arg-Ala -

21                                             30
MAP 30    Phe - Arg - Ala - Thr - Leu - Pro - Phe - Ser - His - Lys -
Tri 1     Leu - Arg - Lys - Ala - Leu - Pro - Asn - Glu - Arg - Lys -
Ric A     Val - Arg - Gly - Arg - Leu - Thr - Thr - Gly - Ala - Asp -

31                                             40
MAP 30    Val - Tyr - Asp - Ile - Pro - Leu-Leu - Tyr - Ser-Thr -
Tri 1     Leu - Tyr - Asp - Leu - Pro - Leu-Ile - Arg - Ser-Ser -
Ric A     Val - Arg - His - Glu - Ile - Pro-Val - Arg - Leu-Pro -

41        44
MAP 30    Ile - Ser - Asp - Pro -
Tri 1     Leu - Pro - Gly - Ser -
Ric A     Leu - Pro - Ile - Asn -
```

FIG. 7
N-TERMINAL AMINO ACID SEQUENCE OF MAP 30 AND ITS COMPARISON WITH TRICHOSANTHIN AND RICIN A CHAIN

```
         1                                                    10
MAP 30   Asp - Val - Asn - Phe - Asp - Leu - Ser - Thr - Ala - Thr -
Tri 1    Asp - Val - Ser - Phe - Arg - Leu - Ser - Gly - Ala - Thr -
Ric A Pro- Ile - Ile - Asn - Phe - Thr - Thr - Ala - Gly - Ala - Thr -

11                                                   20
MAP 30   Ala - Lys - Thr - Tyr - Tyr - Lys - Phe - Ile - Glu - Asp -
Tri 1    Ser - Ser - Ser - Tyr - Gly - Val - Phe - Ile - Ser - Asn -
Ric A    Val - Gln - Ser - Tyr - Thr - Asn - Phe - Ile - Arg - Ala -

21                                                   30
MAP 30   Phe - Arg - Ala - Thr - Leu - Pro - Phe - Ser - His - Lys -
Tri 1    Leu - Arg - Lys - Ala - Leu - Pro - Asn - Glu - Arg - Lys -
Ric A    Val - Arg - Gly - Arg - Leu - Thr - Thr - Gly - Ala - Asp -

31                                                   40
MAP 30   Val - Tyr - Asp - Ile - Pro - Leu - Leu - Tyr - Ser - Thr -
Tri 1    Leu - Tyr - Asp - Leu - Pro - Leu - Ile - Arg - Ser - Ser -
Ric A    Val - Arg - His - Glu - Ile - Pro - Val - Arg - Leu - Pro -

41            44
MAP 30   Ile - Ser - Asp - Pro -
Tri 1    Leu - Pro - Gly - Ser -
Ric A    Leu - Pro - Ile - Asn -
```

PLANT PROTEIN USEFUL FOR TREATING TUMORS AND HIV INFECTION

This application is a continuation of application Ser. No. 08/048,066, filed Apr. 19, 1993, now abandoned, which is a continuation of application Ser. No. 07/594,156, filed Oct. 9, 1990, now abandoned.

FIELD OF THE INVENTION

The present invention in the fields of virology and oncology relates to MAP 30, a protein purified from *Momordica charantia* plant extracts said protein having anti-tumor and anti-HIV activity in vitro, and to uses therefor in treating tumors.

BACKGROUND OF THE INVENTION

Cancer And Approaches To Its Therapy

Cancer results when normal cells undergo neoplastic transformation and develop into malignant tumors. This transformation is due to underlying genetic alterations. Oncogenes are believed to be altered forms of normal genes, called proto-oncogenes, that act as central regulators of growth in normal cells. When a carcinogenic agent such as radiation or a chemical carcinogen, damages the DNA of the target gene of a cell, cancer may develop. Once activated by a mutation, an oncogene may promote excessive or unregulated cell growth. One class of oncogenes acts in normal cells to suppress rather than to promote cell proliferation. A loss of this type of growth suppressor gene from a cell removes a normal constraint on cell growth, leading to uncontrolled proliferation, which in turn may lead to cancer.

Intensive efforts to develop therapies which can prevent or block the development of cancer are currently under way. Historically, efforts have been focused on the treatment of disease using surgery, radiotherapy, and various forms of chemotherapy, to remove or destroy the tumor tissues. The cytotoxic methods are severely limited by their lack of specificity.

Immunotoxins and Their Limitations

Immunotoxins have been developed by conjugating a protein toxin to a tumor-specific monoclonal antibody via a linker for targeted tumor therapy (Vitetta, E. S. et al., *Ann. Rev. Immunol.* 3:197–212 (1985)). In principle, an injected immunotoxin is transported through the blood stream to the targeted tumor tissue, penetrates the tissue, binds to the individual tumor cells, and the toxin acts in a highly localized manner to destroy only the bound tumor cells. All three components of the conjugates are important for the specific delivery of the cytotoxicity: The antibody enables the conjugate to be retained in the target tissue by binding to a specific cell-surface antigen, which enhances cellular uptake by the target cells. The linker keeps the toxin bound to the antibody and inactive while in circulation, but allows for rapid release of the active toxin inside the target cells. The toxin kills the cell by inhibiting cellular protein synthesis, or by some other related mechanism.

Some of the most cytotoxic substances known are protein toxins of bacterial and plant origin (Frankel, A. E. et al., *Ann. Rev. Med.* 37:125–142 (1986)). The cytotoxic action of these molecules involves two events—binding the cell surface and inhibition of cellular protein synthesis. The most commonly used plant toxins are ricin and abrin; the most commonly used bacterial toxins are diphtheria toxin and Pseudomonas exotoxin A.

In ricin and abrin, the binding and toxic functions are contained in two separate protein subunits, the A and B chains. The ricin B chain binds to the cell surface carbohydrates and promotes the uptake of the A chain into the cell. Once inside the cell, the ricin A chain inhibits protein synthesis by inactivating the 60S subunit of the eukaryotic ribosome Endo, Y. et al., *J. Biol. Chem.* 262:5908–5912 (1987)).

Diphtheria toxin and Pseudomonas exotoxin A are single chain proteins, and their binding and toxicity functions reside in different domains of the same protein chain. In diphtheria toxin, the C-terminal domain inhibits protein synthesis by ADP-ribosylation of the elongation factor, EF2. The two activities are separate, and the toxin elicits its full activity only after proteolytic cleavage between the two domains. Pseudomonas exotoxin A has the same catalytic activity as diphtheria toxin.

The use of diphtheria toxin-based immunotoxins is limited by the fact that most people have been immunized against diphtheria toxin. The use of ricin-based immunotoxins is also limited because these immunotoxins exhibit specific toxicity only in the presence of lactose, which at high concentrations competes with the cell surface carbohydrates for the B chain binding sites. An alternative approach has been developed to use ricin A chain or "single chain ribosome inactivating protein" (SCRIP) in the preparation of immunotoxins.

Single Chain Ribosome Inactivating Proteins (SCRIPs) and Their Potential Application in Tumor Therapy SCRIPs are highly active at inactivating ribosomes in cell-free systems, but are relatively nontoxic to intact cells. A wide variety of such molecules are found in plants. These include pokeweed antiviral protein, wheat germ protein, gelonin, dianthins, momorcharins, trichosanthin, and many others (Strip, F. et al., *FEBS Lett.* 195:1–8 (1986)). Some of these SCRIPs have been exploited in the preparation of immunotoxins. Once inside the cell, their cytotoxicity is surprisingly higher than that of the native "holo" counterparts. Many of these SCRIPs are antiviral agents, and some also exhibit specific antitumor activity.

HIV Infection and AIDS

Human Immunodeficiency Virus (HIV), the etiological agent for AIDS (Acquired Immune Deficiency Syndrome), is a member of the lentiviruses, a subfamily of retroviruses. Many retroviruses are well-known carcinogens. HIV per se is not known to cause cancer in humans or other animals, but it does present a formidable challenge to the host. HIV integrates its genetic information into the genome of the host. The viral genome contains many regulatory elements which allow the virus to control its rate of replication in both resting and dividing cells. Most importantly, HIV infects and invades cells of the immune system; it destroys the body's immune system and renders the patient susceptible to opportunistic infections and neoplasms. The immune defect appears to be progressive and irreversible, with a high mortality rate that approaches 100% over several years.

HIV is transmitted by parenteral inoculation and/or intimate sexual contact. It is estimated that about 2 million people in the United States are currently infected with HIV, and 5 to 10 million people are infected worldwide. Recent projections indicate that a majority of those now infected will develop AIDS within a seven year follow-up period. In 1989 alone, over 130,000 cases of AIDS were reported domestically, and more than half of these patients have died. It is estimated that an additional 200,000 cases will be diagnosed in the United States by the end of 1990. Reports to the World Health Organization suggest that at least a million of new cases of AIDS can be expected within the next five years worldwide. It is apparent that AIDS is an unprecedented threat to U.S. as well as global health. The search for effective therapies to treat AIDS is of paramount importance.

HIV-1 is trophic and cytopathic for T4 lymphocytes, cells of the immune system which express the cell surface differentiation antigen CD4 (also known as OKT4, T4 and leu3). The viral tropism is due to the interactions between the viral envelope glycoprotein, gp120, and the cell-surface CD4 molecules (Dalgleish, A. G. et al., *Nature* 312: 763–767 (1984). These interactions not only mediate the infection of susceptible cells by HIV but are also responsible for the virus-induced fusion of infected and uninfected T cells. This cell fusion results in the formation of giant multinucleated syncytia, cell death, and progressive depletion of CD4 cells in AIDS patients. These events result in HIV-induced immunosuppression and its subsequent sequelae, opportunistic infections and neoplasms.

In addition to CD4+ T cells, the host range of HIV includes cells of the mononuclear phagocytic lineage (Dalgleish, A. G. et al., supra), including blood monocytes, tissue macrophages, Langerhans cells of the skin and dendritic reticulum cells within lymph nodes. HIV is also neurotropic, capable of infecting monocytes and macrophages in the central nervous system causing severe neurologic damage. Macrophage/monocytes are a major reservoir of HIV. They may interact and fuse with CD4-bearing T cells, causing T cell depletion and thus contributing to the pathogenesis of AIDS.

Anti-HIV Drugs

Intensive efforts are currently under way to develop therapies to prevent or intervene in the development of clinical symptoms in HIV-infected individuals. For the most part, efforts have been focused on the use of nucleoside analogue drugs such as AZT (azidothymidine), and on other dideoxynucleoside derivatives such as ddA (dideoxyadenosine), ddT (dideoxythimedine), ddI (dideoxyinosine), and ddC (dideoxycytidine). These drugs inhibit the viral enzyme, reverse transcriptase, thereby inhibiting de novo infection of cells. However, once viral infection has been established within a cell, viral replication utilizes host cell enzymes. Thus, drugs which inhibit only reverse transcriptase would be expected to have limited effects. While the spread of free virus within the organism may be blocked, the mechanisms of syncytium formation and pathogenesis through direct intercellular spread remain.

A very small number of HIV-infected T cells can fuse with, and eventually kill, large numbers of uninfected T cells through mechanisms based on viral surface antigen expression. In vitro studies have demonstrated HIV replication even in the continued presence of nucleoside analogues in prolonged culture. Drugs targeting other viral processes are also being developed, such as soluble CD4 and dextran sulfate to inhibit viral binding, alpha interferons and "ampligen" to inhibit viral budding, and castanospermine to inhibit the processing of the viral glycoproteins. These drugs are still in early stages of testing. The actual processes of HIV intracellular replication and protein synthesis have not been specifically targeted because these viral functions were thought to reflect the mere pirating of normal host processes through host mechanisms.

Recently, M. S. McGrath et al. (*Proc. Natl. Acad. Sci. USA* 86:2844–2848(1989)) reported that GLQ 223, a SCRIP isolated from the Chinese medicinal plant, *Trichosanthis kirilowii*, selectively inhibits HIV replication. This compound demonstrated dose-dependent anti-HIV activity in both acutely and chronically infected T cells, as well as in monocytes/macrophages. This discovery has led to the rapid clinical testing of GLQ 223 as an anti-AIDS drug. Treatment of cells with GLQ 223 resulted in selective inhibition of the synthesis of viral DNA, RNA, and protein, with little or no effect on cellular synthesis. Inhibition of viral replication occurred at GLQ 223 concentrations that had no detectable effect on uninfected cells.

The mechanisms of the selective anti-HIV activity of GLQ 223 is not known. It has not been established whether this activity is associated with the ribosome-inactivating or the abortifacient activity of this compound. Two possible mechanisms are immediately apparent. Selective binding or uptake of GLQ 223 by infected cells could be responsible for its selective action on infected cells. Once inside the infected cells, the compound could act non-specifically, via its ribosome inactivating function. Alternatively, selectivity of the agent may arise from differential effects on viral versus cellular components, resulting in inhibition of viral but not of cellular nucleic acid and protein synthesis.

Lifson et al., U.S. Pat. No. 4,795,739 (issued Jan. 3, 1989), discloses that plant proteins, including trichosanthin and alpha and beta Momorcharin (also known as Momorcharin A and B, or MCA and MCB), reduce viral antigen expression in HIV-infected cells, and are selectively toxic to HIV-infected cells. These proteins are said to be useful for treating HIV infections in humans.

SUMMARY OF THE INVENTION

It is an object of the present invention to overcome the aforementioned deficiencies of the prior work.

It is an object of the present invention to provide a protein obtainable from both the fruit and the seed of the plant *Momordica charantia* which has both anti-tumor and anti-HIV activity, substantially free of other plant-derived contaminants, or a functional derivative thereof.

In one embodiment, the protein is purified from the plant material; alternatively, it is produced by recombinant DNA means.

In a preferred embodiment, the protein, MAP 30, has a molecular weight of about 30 kD as determined by SDS polyacrylamide gel electrophoresis and has an N-terminal amino acid sequence:

```
         1              5                   10                  15           (SEQ. ID NO: 1)
    H2N—Asp—Val—Asn—Phe—Asp—Leu—Ser—Thr—Ala—Thr—Ala—Lys—Thr—Tyr—Thr—

20                   25                  30
    Lys—Phe—Ile—Glu—Asp—Phe—Arg—Ala—Thr—Leu—Pro—Phe—Ser—His—Lys—

35                   40           44
    Val—Tyr—Asp—Ile—Pro—Leu—Leu—Tyr—Ser—Thr—Ile—Ser—Asp—Pro—COOH
```

The invention also provides a process for purifying a protein having both anti-tumor and anti-HIV activity from the fruit or seeds of the plant *Momordica charantia*, comprising (a) homogenizing the fruit or seed resulting in a homogenate;

(b) centrifuging the homogenate at least once, and recovering the supernatant; and (c) fractionating the supernatant and recovering the protein.

The invention is further directed to a DNA sequence encoding the amino acid sequence of the above-described protein or of a functional derivative thereof, substantially free of other DNA sequence. The DNA is preferably genomic DNA or cDNA. The DNA sequence preferably comprises an expressible vehicle.

The invention also provides prokaryotic and eukaryotic host cells transformed or transfected with the above DNA.

Also provided is a substantially pure protein encoded by the DNA expressed in a prokaryotic or eukaryotic host.

The present invention also provides improved methods for treating a subject with a tumor. More specifically, the invention is directed to a method for treating a subject infected with a tumor comprising administering to the subject an effective amount the protein of the invention or a functional derivative thereof.

The invention is also directed to a method for treating a subject with a tumor by administering the MAP 30 protein in combination with any one or more of the known anti-AIDS therapeutics, including, but not limited to, AZT, ddI, soluble CD4, ddC, ddA, and GLQ 223.

The treatment methods of the invention also includes administering to a subject a conjugate of MAP 30 with soluble CD4 or CD4 derivatives, or antibodies specific for CD4 or HIV-coded glycoproteins such as gp120 and gp41.

The invention also provides a method for treating a subject having a tumor comprising administering an effective amount of the protein of the invention or a functional derivative thereof, either alone or, preferably, in combination with a tumor-specific antibody or other tumor-directing agent.

BRIEF DESCRIPTION OF THE DRAWINGS

FIG. 7 shows the sequence of the N-terminal 44 amino acids of MAP 30 and a comparison with the N-terminal sequence of trichosanthin (Tri-1) and ricin A chain (Ric A) residues 7 to 51 as reported by Zhang et al. (Nature 321:477–478 (1986)). Boxed regions are identical or conserved amino acids of these plant proteins. Substitutions of amino acid with similar physicochemical properties are taken as conservative as with Ser and Thr, Val, Leu, and Ile, Asp and Glu.

DETAILED DESCRIPTION OF THE INVENTION

The plant proteins of the present invention, which are distinct from GLQ 223, belong to the family of ribosome-inactivating proteins.

*Momordica charantia*, also known as Mubie or MC, is the source material for the isolation of the MAP 30 protein. The fruit and seeds of this plant are known as "kugua" and "kuguazi," respectively. *Momordica charantia* grows widely in southern and eastern China from April to September, with the peak harvest in midsummer.

There are many varieties of *Momordica charantia,* some of which are grown primarily for medicine, while others also serve as vegetable and fruit for eating. The content of MAP 30 is most abundant in the medicinal variety, which has not been naturally available in the United States. In oreder to provide a constant and sufficient supply of the source material for the inventors' experiments, they began planting and cultivating the medicinal variety from selected seeds.

Figure 1A:
FIG. 1 is a photograph of a *Momordica charantia* plant with its fruits. Panel A shows an immature fruit in its characteristic green color. Panel B shows a ripened fruit with bright orange outer skin and red seed.
Figure 1B:

Seeds are planted and germinated after 14–20 days. Plants begin to bear fruit after 60–80 days, and the fruits mature to ripeness by about 90–120 days. Extract are prepared from various parts of the plant, particularly fruit and seeds, at different stages of maturation. A potent anti-HIV active component is present in the fruit and seed, and its content increases significantly with the maturity of the fruit and seed. A growing *Momordica charantia* fruit is shown in FIG. 1A; the fruit is green in color. As the fruit matures, its color turns to a light yellow and finally bright orange as it reaches full maturity. If the fruits are not harvested by this stage, they split open spontaneously, exposing the matured red seeds, as shown in FIG. 1B. Naturally ripened fruits and seeds are preferred for preparation of MAP 30.

By the term "anti-tumor activity" is intended the ability to inhibit the growth of tumor cells in vitro or in vivo, to inhibit the development of a tumor in vivo from a tumor cell which has undergone tumorigenic transformation in vivo in the subject animal or from a tumor cell which has been implanted in the animal. This term is intended to encompass the actual oncogenic transformation of a cell to become tumorigenic, as well as the ability of a tumor cell to metastasize to or invade an alternate site in the body.

The antitumor activities of the momorcharin family of proteins have been confirmed by independent testing; this type of activity is well known in the art.

The MAP 30 protein is used for treatment either alone, or in combination with other modes of therapy known in the art, including chemotherapy with drugs, such as AZT, ddC, ddA, ddT ddI, GLQ 223 or with biologically based therapy, as with soluble CD4, for example.

By the term "anti-HIV activity" is intended the ability to inhibit viral attachment to cells, viral entry into cells, and cellular metabolism which permits viral replication, production and release. Also intended is the inhibition of intercellular spread of the virus. The term is meant to encompass inhibition of synthesis and cellular expression of viral antigens, activity of virus-coded enzymes such as reverse transcriptase and protease, and all known HIV pathogenic actions, such as, for example, immunosuppression. Thus, any activity which tends to inhibit any of these mechanisms is "anti-HIV activity."

By "functional derivative" is meant a "fragment," "variant," "analog," or "chemical derivative" of MAP 30 which , terms are defined below. A functional derivative retains at least a portion of the function of MAP 30 which permits its utility in accordance with the present invention.

A "fragment" of MAP 30 refers to any subset of the molecule, that is, a shorter peptide.

A "variant" of MAP 30 refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., *DNA* 2:183 (1983)) of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

An "analog" of MAP 30 refers to a non-natural molecule substantially similar to either the entire molecule or a fragment thereof.

A "chemical derivative" of MAP 30 contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980)

For purification of the MAP 30 protein of the present invention, chromatography on CM-Sepharose CL6B ("Step 2") can be used following the appropriate extraction procedures. As is readily apparent to one skilled in the art, effective fractionation depends on the optimum design of the experimental conditions in terms of the capacity of the exchanger, the size of the column, the amount of the sample, and the elution conditions.

For example, for 100 grams of starting material, a column size of approximately 1.5×40 cm (70 ml) is preferably used. The column is equilibrated with the starting buffer B. The sample in the same buffer is cleared by centrifugation to remove any precipitate which formed during dialysis or storage. The column is washed with the starting buffer until a baseline absorbance reading is reached. The elution is monitored by UV absorption at $A_{280}$.

A linear gradient consisting of 240 ml of solution B and 240 ml of 0.2M NaCl in solution B can then be applied. Six ml fractions are collected using a fraction collector. Fractions are tested for their anti-HIV activity as described herein. MAP 30 is eluted at salt concentrations of 60 to 70 mM. Active fractions are pooled, buffer changed and concentrated by Centricon 10 (Amicon, 10,000 Mr exclusion).

Gel filtration is then performed using Sephadex G75 Superfine in 20 mM sodium phosphate, pH 6.3 with a column size of 1.5×110 cm. A sample from step 2 is buffer-changed to 20 mM sodium phosphate, pH 6.3 and concentrated to about 2 ml by Centricon-1 prior to being loaded on the column. The column is eluted with the same buffer. The anti-HIV activity is eluted as a single major peak in this way (see Examples).

Homogeneous samples are used for structural and functional characterization using tryptic analysis, amino acid sequencing, antibody production, and assessment of biological activity, such as inhibition of in vitro protein synthesis (ribosome inactivation), and anti-HIV replication.

Genomic and cDNA clones encoding SCRIP from *Momordica charantia* are cloned based on knowledge of partial amino acid sequences. Oligonucleotide primers designed from these sequences are used in the polymerase chain reaction (PCR) to specifically amplify the SCRIP genes using two methods.

In the first method, two primers encoding two ends of the SCRIP peptide are used in PCR with poly (A+) mRNA and genomic DNA as template. The genomic or cDNA fragment thus amplified are cloned into the plasmid pUC18, making use of restriction sites added to the 5'-end of the oligonucleotide primers. This method requires very little starting material for use as a template.

In the second method, a single specific primer is used. Lambda phage libraries generated from genomic DNA or cDNA are used as template. Using the PCR reaction to amplify specific clones is more sensitive than directly screening the plated libraries with labelled oligonucleotide. Phage DNA from the libraries is prepared from a plate lysate, and the mixture is used as a template in PCR. One of the primers is designed from the specific amino acid sequence of the SCRIP, and the other primer is complementary to the lambda phage vector near one end of the cloning site. With appropriate stringency in the PCR conditions, few specific clones should be amplified. In this method, only one specific primer is necessary.

High molecular weight genomic DNA is isolated from *Momordica charantia*. The procedure is similar for fresh and frozen *Momordica charantia* fruit and seeds.

There are several problems unique to isolation of nucleic acids from plant tissues. First, the plant cell wall is difficult to disrupt without shearing high molecular weight DNA. Second, crude plant extracts contain large quantities of polysaccharides, tannins, and pigments which copurify with nucleic acids and interfere with subsequent analysis and enzymatic manipulation.

Frozen tissue can be homogenized without damage to high molecular weight DNA by blending into a dry powder in a Waring blender in the presence of liquid nitrogen. For example, for isolation of genomic DNA, 5 grams of powdered plant tissue are resuspended in a 50 ml extraction buffer consisting of 100 mM Tris HCl pH 8.0, 0.7M NaCl, 10 mM EDTA, 1% 2-mercaptoethanol, and 1% (w/v) cetyl triammonium bromide (CTAB), and incubated at 55° C. for 30 minutes. The detergent CTAB efficiently disrupts the cell wall and forms a soluble complex with nucleic acids in the presence of the high salt (0.7M NaCl). The mixture is then cooled to room temperature and extracted twice with chloroform/isoamyl alcohol. The aqueous layer was centrifuged at 155 x g for 10 minutes, and any precipitate is discarded.

The supernatant is then diluted with an equal volume of precipitation buffer, consisting of 100 mM Tris HCl pH 8.0, 10 mM EDTA, 1% CTAB, and allowed to stand at room temperature for 1 hour. As the salt concentration is reduced below 0.4M NaCl, the CTAB-nucleic acid complex precipitates, leaving the polysaccharides and other contaminants in solution. The mixture is then centrifuged at 155 x g for 30 minutes.

The pellet is resuspended in 10 mM Tris, 1 mM EDTA (TE), and extracted twice with phenol/chloroform, and once with chloroform/isoamyl alcohol. The solution is made 0.3M with sodium acetate, and three volumes of ethanol are layered on top. Genomic DNA is spooled from the solution by stirring with a sterile glass rod. The DNA is rinsed with 70% ethanol, dried briefly, and resuspended in TE at 1 mg/ml. By agarose gel electrophoresis, the size of the DNA prepared in this way has been determined to be over 20 kb. The yield from 5 g of starting material was found to be about 1 mg from *Momordica charantia* fruit and 1.5 mg from seeds.

RNA is prepared from these plant tissues by blending the frozen tissue in the presence of liquid nitrogen into powder, and homogenizing the powder in 10 weight volumes of RNAzol, a commercially available extraction agent which contains guanidine isothiocyanate, SDS, and phenol (Cinna/Biotecx, Texas). The homogenate is expected to contain polysaccharides, and is centrifuged at 2000 x g for 30 minutes at 4° C. The supernatant is carefully removed, leaving behind a gelatinous mass. The supernatant is extracted twice with an equal volume of chloroform; DNA and protein form an insoluble complex at the interface. RNA is precipitated from the aqueous layer with isopropanol. The pellet is resuspended, extracted with phenol:chloroform, and precipitated with ethanol to yield total cellular RNA. Using this method, the yield from 10 grams of starting material was about 1 mg from *Momordica charantia* fruit, and 0.5 mg from seeds. The $A_{260}/A_{280}$ ratio was found to be 1.9 to 2.0.

Poly (A+) RNA is isolated by chromatography on oligo-dT cellulose. Yields of 2–5% of RNA are routinely obtained.

Oligonucleotide primers for PCR are designed from the amino acid sequence of the SCRIP. Because the degeneracy of the genetic code increases the number of possible codon choices at each position, in order to account for every possibility, a mixture of oligonucleotide primers is used. One of these primers is exactly complementary to the gene in that region. Alternatively, the primers are made longer, and each possibility is not accounted for. In this latter case, the length of the primer and the first two bases of each codon confer the specificity required. Although the exact complement of the gene is not present, the primer is sufficiently specific for use in the PCR.

The preferred primers have a length of 17 to 20 nucleotides, initially, with degeneracy of 1024 or less. A hexanucleotide containing a restriction fragment recognition site, such as HindIII, is added to the 5'-end of the primers for use in cloning.

The following 17-base oligonucleotide primers/probes have been designed based on the N-terminal amino acid sequence information of MAP 30. These oligonucleotides have a degeneracy of 64:

```
                                                      SEQ ID NO: 2
Residue  Asp —Val —Asn —Phe —Asp —Leu
     5'  GAT—GTT—AAT—TTT—GAT—CT              3'
           C   C    C    C    C
               A
               G 3'  CTA—CAA—TTA—AAA—CTA—GA              5'
           G   G    G    G    G
               T
               C
```

The following 24-base oligonucleotides complementary to the β-galactosidase gene near the EcoR1 cloning site have been used as primers in PCR:

| | |
|---|---|
| Lambda 1 5' GGTGGCGACGACTCCTGGAGCCCG 3' | SEQ ID NO: 3 |
| Lambda 2 5' TTGACACCAGACCAACTGGTAATG 3' | SEQ ID NO: 4 | cDNA and genomic libraries are cloned into lambda gt11 vector using established methods. Use of the EcoR1 site of gt11 offers specific advantages, as it is possible to use one primer complementary to the β-galactosidase gene adjacent to the cloning site to amplify specific clones, using another primer complementary to the specific gene, in this case, the SCRIP.

cDNA synthesis was done according to the procedure of Gubler and Hoffman (*Gene* 25:263 (1983). First strand cDNA was synthesized using poly (A+) RNA as template and using murine Moloney leukemia virus reverse transcriptase with oligo-dT as primer. Second strand cDNA was made using DNA Polymerase I and *E. coli* ligase in the presence of RNAse H. Double-stranded cDNA is made blunt ended with T4 polymerase, and the resulting cDNA was treated with EcoR1 methylase. EcoR1 linkers were then added, and the cDNA was ligated to lambda gt11 arms and packaged into phage.

Genomic DNA was partially digested with MBoI and size-selected for fragments of 15–23 kb by preparative agarose gel electrophoresis. These fragments were then made blunt-ended, treated with EcoR1 methylase, and cloned into lambda gt11 with EcoR1 linkers.

In conjunction with a singe sequence-specific primer, these lambda primers have been used to amplify specific clones from genomic and cDNA libraries, as well as to obtain overlapping clones which encode areas outside of known nucleotide sequences. Oligonucleotides are synthesized using an Applied Biosystems 380B synthesizer using the phosphorimidate method, and purified using HPLC. A 5' phosphate group is added using T4 kinase.

Using the two primer approach, both oligonucleotides are designed to encode separate portions of the SCRIP peptide. The template is either genomic DNA or cDNA. Using the one primer method, the other primer is a lambda primer and the template is a mixture of phage DNA isolated from the libraries.

Reviews of the polymerase chain reaction are provided by Mullis, K. B. (*Cold Spring Harbor Symp. Quant. Biol.* 51:263–273 (1986)); Saiki, R. K., et al. (*Bio/Technology* 3:1008–1012 (1985)); and Mullis, K. B., et al. (*Met. Enzymol.* 155:335–350 (1987)).

PCR reaction condition variables include annealing temperature, polymerization time, and ratio of template to primers. In one embodiment, 100 ng of cDNA or 1 μg of total genomic DNA or mixed phage library DNA is used as template. Then, 5–100 pmol of oligonucleotide primer is used, depending upon the degeneracy of the primer. PCR reactions are carried out in a programmable thermal cycler.

A typical cycle consists of 94° C. denaturation for 1 minute, 45° C. annealing for 2 minutes, and 72° C. polymerization for 3 minutes for the first 20 cycles, followed by an additional 20 cycles during which the polymerization time is incrementally increased by two seconds each cycle. Reaction products are analyzed by agarose gel electrophoresis using conventional agarose for products 500 bp to several kilobases, and NuSieve agarose for products 100 bp to 2 kb.

The genomic or cDNA fragment thus amplified is cloned making use of restriction sites added to the 5'-end of the oligonucleotide primers. The PCR reaction products are digested with restriction enzyme, and cloned into a pUC18 vector which has been linearized at the appropriate site and treated with calf intestinal phosphatase. These clones are then screened using radiolabelled gel-purified DNA corresponding to the major PCR products.

These clones are used to screen genomic and cDNA lambda phage libraries for overlapping clones. In addition, sequence information from these clones is used to design new primers for single-primer PCR amplification from phage libraries. Alternatively, primer extension using sequences derived from these clones is used to generate full length cDNA clones.

Techniques for synthesizing such oligonucleotides are also disclosed by, for example, Wu, R., et al., *Prog. Nucl. Acid. Res. Molec. Biol.* 21:101–141 (1978)). Procedures for constructing recombinant molecules in accordance with the above-described methods are disclosed by Sambrook, J. T. et al., *Molecular Cloning: A Laboratory Manual,* Second Ed., Cold Spring Harbor Press, Cold Spring Harbor, N.Y. (1984). These two references are herein incorporated by reference.

The cloned genes for MCI, MCA, MCB and MAP 30, can be expressed in prokaryotic expression vectors or in eukaryotic expression vectors, which are known in the art.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing the plant protein of the invention in order to produce a prokaryotic genomic expression vector library. Procedures for preparing cDNA and for producing a genomic library are disclosed by Sambrook et al., (supra).

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a sequence encoding the desired protein) are said to be "operably linked" if the nature of the linkage between the two DNA sequences does not (1) result in the introduction of a frame-shift mutation, (2) interfere with the ability of the promoter region sequence to direct the transcription of the gene to be expressed, or (3) interfere with the ability of the gene sequence which is to be expressed to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to utilize (i.e. transcribe) only one strand of the two strands of a duplex DNA template. The selection of which strand is transcribed is determined by the orientation of the promoter sequence. This selection determines the direction of transcription since RNA is only polymerized enzymatically by the addition of a nucleotide 5' phosphate to a 3' hydroxyl terminus.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987); Hu, M. et al., *Gene* 42:21–30 (1986)), T3, Sp6, and T7 (Chamberlin, M. et al., *Nature* 228:227–231 (1970); Bailey, J. N. et al., *Proc. Natl. Acad. Sci. (U.S.A.)* 80:2814–2818 (1983); Davanloo, P. et al., *Proc. Natl. Acad. Sci. (U.S.A.)* 81:2035–2039 (1984)) polymerases; the $P_R$ and $P_L$ promoters of bacteriophage 1 (*The Bacteriophage Lambda*, Hershey, A. D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the trp, recA, heat shock, and lacZ promoters of *E. coli;* the a-amylase (Ulmanen, I., et al., *J. Bacteriol.* 162:176–182 (1985)) and the s-28-specific promoters of *B. subtilis* (Gilman, M. Z., et al., *Gene* 32:11–20 (1984)); the promoters of the bacteriophages of Bacillus (Gryczan, T. J., In: *The Molecular Biology of the Bacilli*, Academic Press, Inc., N.Y. (1982)); Streptomyces promoters (Ward, J. M., et al., *Mol. Gen. Genet.* 203.:468–478 (1986)); the int promoter of bacteriophage l; the bla promoter of the b-lactamase gene of pBR322, and the CAT promoter of the chloramphenicol acetyl transferase gene of pPR325, etc. Prokaryotic promoters are reviewed by Glick, B. R., (*J. Ind. Microbiol.* 1:277–282 (1987)); Cenatiempo, Y. (*Biochimie* 68:505–516 (1986)); Watson, J. D. et al. (In: *Molecular Biology of the Gene*, Fourth Edition, Benjamin Cummins, Menlo Park, Calif. (1987)); and Gottesman, S. (*Ann. Rev. Genet.* 18:415–442 (1984)). Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); and the yeast gal4 gene promoter (Johnston, S. A., et al., *Proc. Natl Acad Sci (USA)* 79:6971–6975 (1982); Silver, P. A., et al., *Proc. Natl. Acad. Sci. (USA)*. 81:5951–5955 (1984)). All of the above listed references are incorporated by reference herein.

Production of the plant proteins of the present invention or functional derivatives thereof in insects can be achieved, for example, by infecting the insect host with a baculovirus engineered to express the gene of interest by methods known to those of ordinary skill in the art. Thus, in one embodiment, sequences encoding MAP 30 may be operably linked to the regulatory regions of the viral polyhedrin protein (Jasny, *Science* 238:1653 (1987)). Infected with the recombinant baculovirus, cultured insect cells, or the live insects themselves, can produce the MAP 30 protein in amounts as great as 20 to 50% of total protein production. When live insects are to be used, caterpillars are presently preferred hosts for large scale protein production according to the invention.

Strong promoters are the most preferred promoters of the present invention. Examples of such preferred promoters are those which recognize the T3, SP6 and T7 polymerase promoters; the $P_L$ promoter of bacteriophage lambda; the recA promoter and the promoter of the mouse metallothionein I gene.

Expression of the cloned genes encoding the proteins of this invention permits the large scale production of the active proteins. New chimeric molecules can then be created with enhanced anti-tumor and/or anti-viral activity and less toxicity to the host cells, using only the parts of the molecule that are active against viruses or tumors. For example, the plant proteins of the present invention may be coupled to other proteins having inhibitory and cytotoxic properties, including, but not limited to Ricin A chain, Pseudomonas toxin, Diphtheria toxin, and tumor necrosis factor. Toxins conjugated to antibodies or other ligands, are known in the art (see, for example, Olsnes, S. et al., *Immunol. Today* 10:291–295 (1989)). Such coupling may be achieved by chemical means or by recombinant DNA techniques wherein DNA encoding MAP 30 is linked with DNA encoding another toxic protein, a CD4 molecule or fragment, a monoclonal antibody chain or fragment, such as the heavy chain variable region, and the like.

SCRIPs inhibit protein synthesis by hydrolytic cleavage of a glycosidic linkage between the adenine and the ribose at a specific site $A_{4324}$ on the 28S rRNA, leaving the phosphodiester bonds of the RNA backbone intact. This reaction results in a decrease in the stability of the RNA and renders it sensitive to aniline treatment at pH 4.5, with a fragment of about 450 nucleotides being liberated on cleavage. These same results were observed with treatment of either native ribonuclear protein particles, or naked 28S rRNA. This direct interaction of SCRIPs with naked rRNA affects the stability of cellular RNA upon SCRIP treatment.

Additional conjugates of MAP 30 or a functional derivative thereof, contemplated within the scope of the present invention, include conjugates with antibodies specific for tumor antigens or HIV antigens, such as gp120 or gp41 (Matsushita, S. et al., *AIDS Res. Hum. Retroviruses* 6:193–203 (1990), which is hereby incorporated by reference), conjugates with CD4 molecules or soluble CD4 fragments, and the like. Such conjugates will allow the targeted delivery of MAP 30 to a site of interest, such as a cell expressing an HIV antigen, to achieve even greater specificity and lower nonspecific toxicity.

The present invention also provides a method for recombinant engineering of the cells of an AIDS patient for in situ expression of MAP 30. A hybrid plasmid containing the MAP 30 gene or a fragment thereof under the direction of the HIV LTR may be inserted into a retroviral vector. For a discussion of the methods involved in retroviral vector production and expression, see, for example, Palmer, T. D. et al., *Proc. Nat'l. Acad. Sci. USA* 84:1055–1059 (1987); Wilson, J. M. et al., *Proc. Nat'l. Acad. Sci. USA* 85:3014–3018 (1988); Zwiebel, J. A. et al., *Science* 243:220–222 (1989), which references are hereby incorporated by reference). Transfected cells containing an integrated HIV-MAP 30 plasmid would express very low levels of MAP 30 constitutively; however, upon transactivation with HIV infection, production of MAP 30 would be efficiently induced. The continuous presence of MAP 30, endogenously supplied, may have therapeutic benefits beyond those achieved by conventional administration of the protein.

To treat patients with tumors using the plant proteins according to the present invention, MAP 30, or a functional derivative thereof, is administered to a patient in daily doses ranging from about 1 ng to about 50 mg, more preferably in a range of about 1 µg to about 10 mg. The optimum dosage can best be determined by the practitioner, based in part upon the patient's condition, weight, and response to treatment.

Alternatively, the MAP 30 or a functional derivative thereof is administered as above alternating with GLQ 223 in the same dosages. This combined treatment has been shown to be effective for trophoblastic tumors.

To treat an HIV infection in a subject, MAP 30, or a functional derivative thereof, is administered to a patient in daily doses ranging 1 ng to about 50 mg, more preferably in a range of about 1 µg to about 10 mg.

It is understood that the dosage of MAP 30 and functional derivatives thereof will be dependent upon the age, sex, health, and weight of the recipient, kind of concurrent treatment, if any, frequency of treatment, and the nature of the effect desired. The ranges of effective doses provided herein are not intended to limit the inventors and represent preferred dose ranges. However, the most preferred dosage will be tailored to the individual subject, as is understood and determinable by one of ordinary skill in the art without undue experimentation.

Alternatively, a subject with HIV infection or with AIDS is treated with the above amounts of plant proteins in conjunction with other known therapeutics, including, but not limited to, AZT, ddI, ddA, ddC, GLQ 223 or soluble CD4. Preferably, the drugs are administered on alternate days in the recommended amounts of each drug.

MAP 30 is administered in compositions including compositions wherein the plant protein is contained in an effective amount to achieve its intended purpose. Determination of the effective amounts is well within the skill in the art.

The MAP 30 protein or pharmaceutical compositions of the present invention may be administered by any means that achieve their intended purpose. For example, administration may be by parenteral routes, including subcutaneous, intravenous, intradermal, intramuscular, intraperitoneal, intrathecal, transdermal, or buccal routes. Alternatively, or concurrently, administration may be by the oral or rectal route. The proteins and pharmaceutical compositions can be administered parenterally by bolus injection or by gradual perfusion over time.

In addition to MAP 30 or functional derivative thereof, these pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.1 to about 99 percent, preferably from about 25–85 percent, of active compound(s), together with the excipient.

The pharmaceutical compositions of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture and processing the mixture of granules, after adding suitable auxiliaries, if desired or necessary, to obtain tablets or dragee cores.

Suitable excipients are, in particular, fillers such as sugars, such as lactose, sucrose, mannitol, or sorbitol; cellulose preparations and/or calcium phosphates, such as tricalcium phosphate or calcium hydrogen phosphate; as well as binders such as starch paste made using, for example, maize starch, wheat starch, rice starch, potato starch, gelatin, gum tragacanth, methyl cellulose, hydroxypropylmethylcellulose, sodium carboxymethylcel-lose, and/or polyvinylpyrrolidone.

If desired, disintegrating agents may also be added, such as the above-mentioned starches as well as carboxymethyl starch, cross-linked polyvinyl pyrrolidone, agar, or alginic acid or a salt thereof, such as sodium alginate.

Auxiliaries which can be used in the compositions according to the present invention include flow-regulating agents and lubricants such as silica, talc, stearic acid or salts thereof, and/or polyethylene glycol.

Dragee cores are provided with suitable coatings which, if desired, are resistant to gastric juices. For this purpose, concentrated sugar solutions may be used, which may optionally contain gum arabic, talc, polyvinyl pyrrolidone, and the like.

Also included within the scope of the present invention is an antibody specific for MAP 30 or specific for a functional derivative thereof.

The term "antibody" refers both to monoclonal antibodies which are a substantially homogeneous population and to polyclonal antibodies which are heterogeneous populations. Polyclonal antibodies are derived from the sera of animals immunized with an antigen. Monoclonal antibodies (mAbs) to specific antigens may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, IgD and any subclass thereof.

The term "antibody" is also meant to include both intact molecules as well as fragments thereof, such as, for example, Fab and $F(ab')_2$, which are capable of binding antigen. Fab and $F(ab')_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and $F(ab')_2$ and other fragments of the antibodies useful in the present invention may be used for the detection and quantitation of MAP 30 in the same manner as an intact antibody. Such fragments are typically produced by proteolytic cleavage, using enzymes such as papain (to produce Fab fragments) or pepsin (to produce $F(ab')_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopic determinants usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect the presence of MAP 30. For example, it would be of benefit to monitor the level of MAP 30 in the circulation or in the tissues of a subject receiving therapeutic doses of the protein. Thus, the antibodies (of fragments thereof) useful in the present invention may be employed histologically to detect or visualize the presence of MAP 30.

An assay for MAP 30 typically comprises incubating a biological sample from the subject in the presence of a detectably labeled antibody or antibody fragment capable of identifying MAP 30 and detecting the antibody which is bound in the sample.

Thus, in this aspect of the invention, a biological sample may be treated with nitrocellulose, or other solid support which is capable of immobilizing cells, cell particles or soluble proteins. The support may then be washed with suitable buffers followed by treatment with the detectably labeled MAP 30-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody.

The binding activity of an anti-MAP 30 antibody may be determined according to well known methods, such as enzyme immunoassay (EIA) or radioimmunoassay (RIA). Those skilled in the art will be able to determine operative and optimal assay conditions for each determination by employing routine experimentation.

For EIA, the antibody is detectably labeled by linking to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the antibody or fragments, it is possible to detect binding to MAP 30 through the use of a RIA. A good description of RIA may be found in *Laboratory Techniques and Biochemistry in Molecular Biology*, by Work, T. S., et al., North Holland Publishing Company, NY, (1978) with particular reference to the chapter entitled "An Introduction to Radioimmune Assay and Related Techniques" by Chard, T., incorporated by reference herein.

The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerytherin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The following examples are intended to be illustrative, but not to limit, the invention.

EXAMPLE I

Preparation of MAP 30

For routine preparation of MAP 30, 100–200 grams of *Momordica charantia* seeds were used. The seeds were first decorticated and pulverized. The seed powder was then extracted with ice-cold 0.15M NaCl (solution A) by homogenizing in a tissue blender for 5 minutes at 5 to 6 ml of solution A per gram of seeds. The pH of the extract was adjusted to 3.6 with 1N HCl. The mixture was stirred gently at 4° C. for 15 minutes. Cell debris were removed by filtration with two layers of cheesecloth, followed by centrifugation at 12,000 x g for 30 minutes. The resulting supernatant often contained a layer of seed fat, which was effectively removed by millipore filtration through a 0.45 μm filter. The cleared supernatant was then fractionated by precipitation with ammonium sulfate at 0–30%, 30–60%, and 60–90% saturations. Anti-HIV activity was found in the 30–60% saturated ammonium sulfate precipitate. In an additional embodiment, the crude extract can be fractionated with 0.8 and 2.0 volumes of cold (–20° C.) acetone.

MAP 30 was found in the precipitate formed by the addition of 2.0 volumes of acetone. Both of these procedures give the same yield of MAP 30.

The precipitate was dissolved in 50 mM sodium phosphate, pH 6.3 (solution B) and dialyzed thoroughly against the same buffer. This material was referred to as "Step 1 sample" and was further purified by chromatography on CM-Sepharose CL6B. Step 1 sample was centrifuged at 15,000 x g for 30 minutes to remove any precipitate formed during dialysis, loaded onto a column of CM-Sepharose CL6B (1.5×34 cm) equilibrated with solution B, and the column washed with solution B until baseline absorbance was reached. About 60–70% of the contaminating proteins were removed, whereas MAP 30 bound to CM-Sepharose CL6B and was thus retained on the column.

Figure 2A:
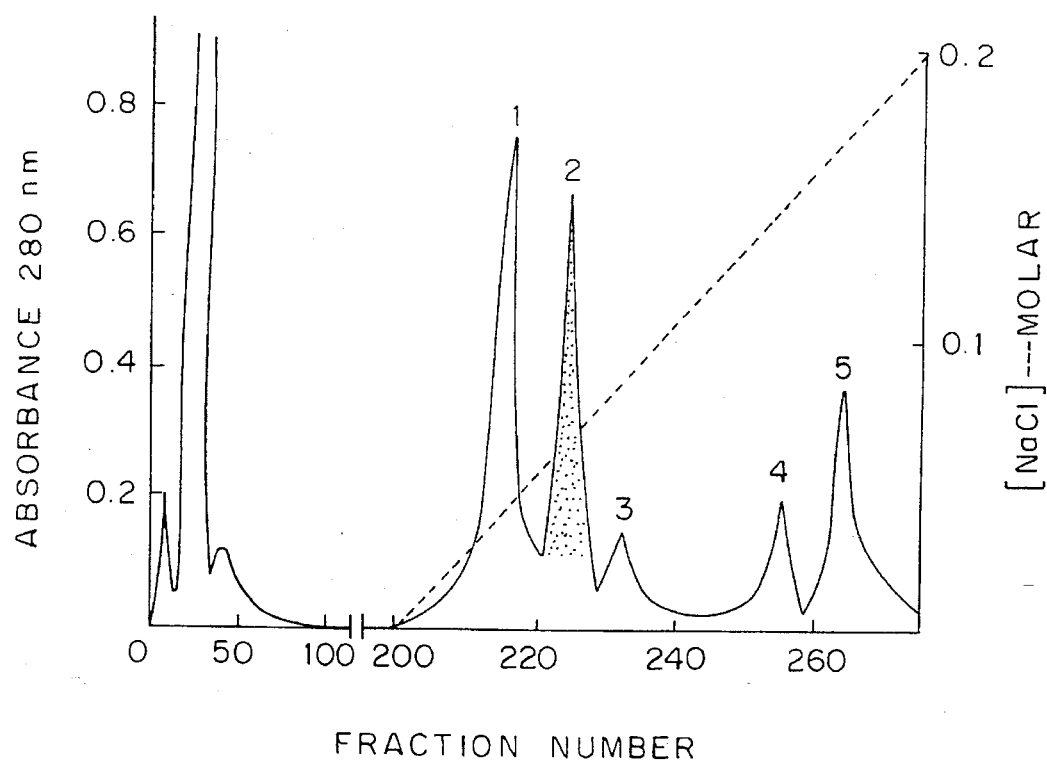
FIG. 2A is a graph depicting the purification of MAP 30 from *Momordica charantia* seed extract. Purification of crude MAP 30 was done using CM-Sepharose CL6B. Step 1 sample was centrifuged at 15,000 xg for 30 minutes to remove any precipitate formed during dialysis. The sample (153 mg) was then loaded onto a column (1.5×34 cm) of CM-Sepharose CL6B (Pharmacia-LKB) equilibrated with 50 mM sodium phosphate, pH 6.3 (solution B). The column was washed with solution B to remove unbound impurities. Whereas MAP 30 bound to CM-S and was thus retained on the column. Fractions of 6 ml was collected at a flow rate of 36 ml per hour. The elution was monitored by absorbance at 280 nm ($A_{280}$). Upon reaching the baseline absorbance of the solution B wash, the column was then eluted with a linear gradient consisting 240 ml of solution B and 240 ml of buffer B containing 0.2M NaCl. The fractions in each peak were pooled, concentrated, buffer changed to PBS and assayed for anti-HIV activity and ribosome inactivating activity. The bulk of the anti-HIV activity was found in peak 2, which was eluted between 60 to 70 mM NaCl.

The column was then eluted with a linear gradient consisting of 240 ml of solution B and 240 ml of solution B containing 200 mM NaCl. A typical elution profile is shown in FIG. 2A. Five major protein peaks were isolated from the *Momordica charantia* extracts. Each of these proteins was further purified to homogeneity. Their sizes and bioactivity were also studied. The molecular weight of the proteins found in peaks 1, 2, 3, 4, and 5 are 32, 30, 29, 23, and 22 kDa, respectively, as determined by SDS-PAGE. All of these proteins showed varying degrees of inhibition of eukaryotic translation. The bulk of the anti-HIV activity was found in peak 2, corresponding to MAP 30. Peak 3, a minor protein peak corresponding to a 29 kD molecule, demonstrated inhibition of p24 expression and RT production in HIV-infected cells as well. Its N-terminal 39 amino acid sequence is identical to that of MAP 30. The 32, 23, and 22 kD proteins demonstrate less effect on HIV infection or replication under the above mentioned assay conditions. These proteins also have different amino acid sequences, and no homology was found to MAP 30. Most importantly, MAP 30 is not toxic to intact cells whereas the other plant proteins are toxic.

Figure 2B:
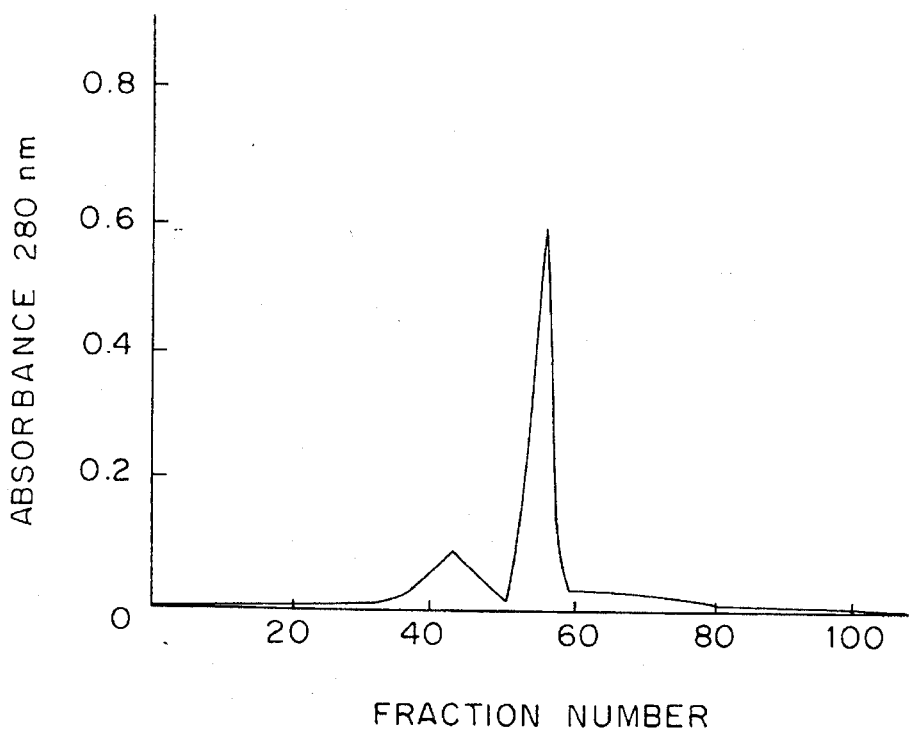
FIG. 2B is a graph depicting further purification of MAP 30 by Sephadex gel filtration. The protein sample pooled from peak 2 of the CM-Sepharose CL6B step (14.5 mg) was further purified by gel filtration on a sephadex G75 superfine column (1.5×110 cm) in 20 mM sodium phosphate buffer, pH 6.3. The elution was monitored by $A_{280}$. The flow rate was 3 ml/hour, and 1.5 ml fractions were collected. Homogeneous MAP 30 was eluted as a single peak from fractions 54 to 58, at about 0.45 column volume.

The majority of the anti-HIV activity was found in peak 2, which was eluted with between 60 and 70 mM NaCl. This material was designated as "step 2 sample," and contained impurities of varying sizes. These contaminants were removed by gel filtration on Sephadex G75 (superfine) in 20 mM sodium phosphate buffer, pH 6.3. As seen in FIG. 2B, MAP 30 was eluted in a single peak at about 0.45 column volume.

Figure 3:
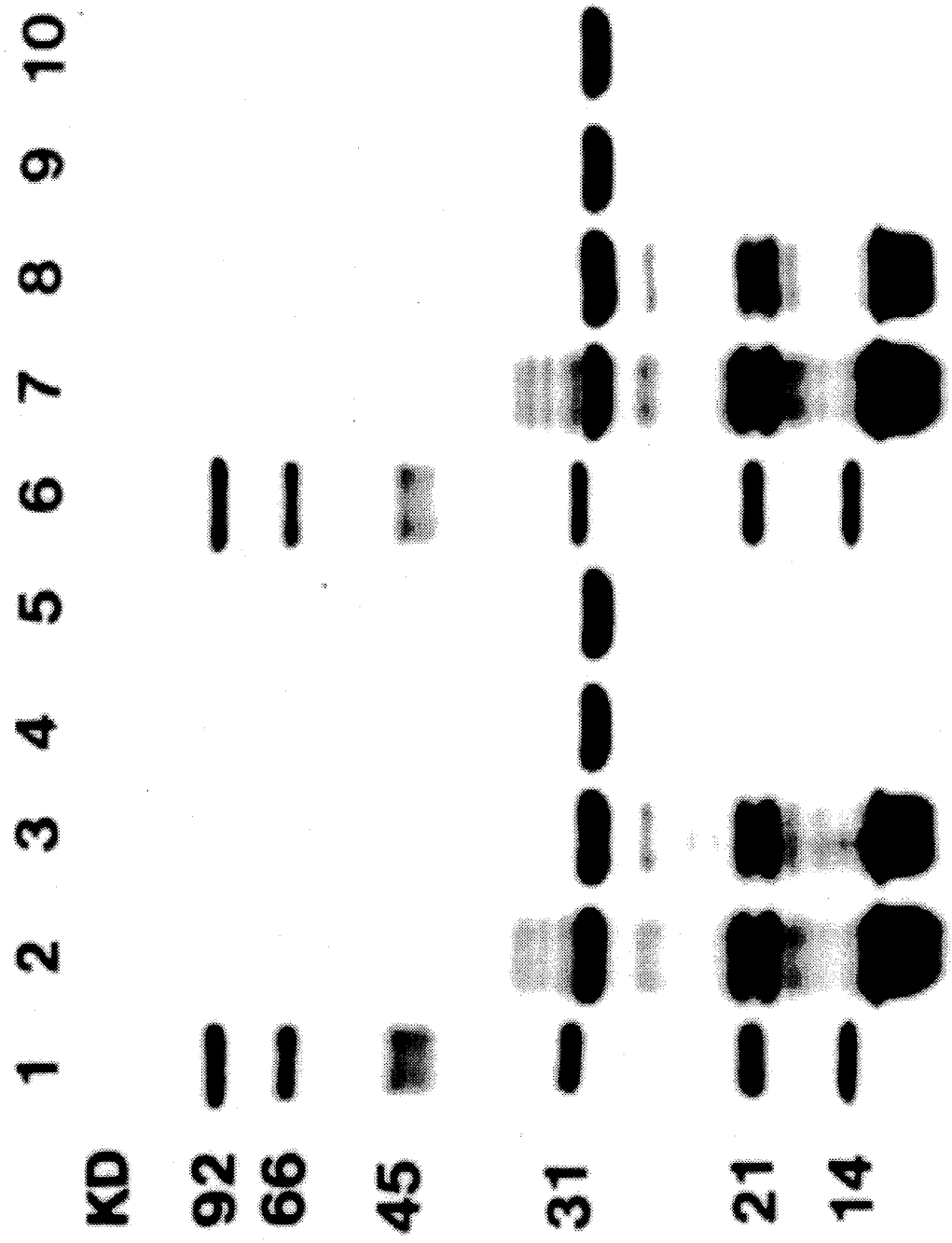
FIG. 3 depicts a gel pattern showing SDS-polyacrylamide gel elecrophoresis (SDS-PAGE) of crude and pure MAP 30 in the presence and absence of the reducing agent, 2-mercaptoethanol. Electrophoresis was carried out at a constant voltage of 80 V for 6 hours, until the tracking dye (bromophenol blue) reached 2 cm from the lower edge of the gel. Lanes 1 to 5 are samples treated with 2-mercaptoethanol: 1, molecular weight standards, 2 μg each; 2, crude MAP 30, 100 μg (30–60% saturated ammonium sulfate fraction); 3, crude MAP 30, 100 μg (2.0 volume acetone precipitate); 4 and 5, homogeneous MAP 30, 8 μg each lane, purified from lanes 2 and 3 respectively. Lanes 6 to 10 are the same corresponding samples as in lanes 1 to 5, but without 2-mercaptoethanol treatment.

The size, homogeneity and subunit structure of MAP 30 were determined by SDS-PAGE in the presence or absence of 2-mercaptoethanol. These results are shown in FIG. 3. A single band with a molecular weight corresponding to 30 kD was obtained for MAP 30 both in the presence (lanes 4 and 5) and absence (lanes 9 and 10) of the reducing agent, indicating that this protein consists of a single chain polypeptide. Lanes 2 and 7 contained crude, while lanes 4 and 9 contained pure, MAP 30 prepared from the 30–60% ammonium sulfate precipitate. Lanes 3 and 8 were loaded with crude, while lanes 5 and 10 had pure, MAP 30 prepared from acetone precipitate (two volumes).

EXAMPLE II

Anti-HIV Activity of MAP 30

Materials and Methods
Cell Lines and Viruses

The CD4 positive T-cell line CEM-ss was used as indicator momolayer cells for the microtiter syncytium-forming assay. The H9 cell line was used in suspension cultures for assays of p24 expression and viral-associated RT activity. HIV-1 virus stock was obtained from R. Gallo. The virus was prepared and stocked as described previously (Nara et al., *AIDS Res. Hum. Retrovir.* 3:283–302 (1987)). The cell lines were maintained in RPMI-1640 with penicillin-streptomycin (100 U/ml) and 10% heat-inactivated fetal calf serum (complete medium).

Purification and Characterization of MAP 30

The conditions for chromatography, and SDS-PAGE are described in the legends to FIGS. 2 and 3. For the preparations of MAP 30 from fruits of *Momordica charantia*, 2 to 5 kg of ripe fruits were used routinely. The fruit juice was adjusted to 0.15M NaCl by the addition of the solid salt. The extraction, fractionation and purification procedures were the same as those described above.

Microtiter Syncytium-Forming Assay

The effect of MAP 30 on the infectivity of HIV-1 was assessed by the quantitative microtiter syncytium-forming infectious cell center assay (SF/ICC) developed by Nara et al. (*Nature* 332:469–470(1988)). The specific experimental conditions are briefly described here. Fresh indicator cells, CEM-SS (syncytium-sensitive Leu-3 positive CEM cell line), in complete RPMI medium were plated onto poly L-lysine coated microtiter wells at 50,000 cells in 50 µl/well. The indicator cells were pre-treated with 50 ul of MAP 30 at concentrations of 1.67, 16.7, 167 and 1670 nM (0.05 to 50 µg/ml) for 15 sec. or 90 min. At the end of these time, 50 µl of a frozen pretitered HIV stock from HxB3/H9 cells, corresponding to one hundred syncytial forming units (SFU) was added to each well for 60 min. The supernatant containing MAP 30 and the virus was then removed from each well and the cells were washed with complete medium to remove residual free of MAP 30 and HIV. The wells were then filled with 200 ul medium or re-fed with medium containing MAP 30 at the same original concentration. The plates were incubated at 37° C. in a humidified incubator at 5% $CO_2$. Focal syncytium formation representing a single infectious virion unit was scored at day 5 (120 hours) by examination under an inverted microscope.

p24 Expression and Reverse Transcriptase Assays

The effect of MAP 30 on HIV-1 replication and transmission in vitro was tested by assaying viral core protein p24 expression and viral reverse transcriptase (RT) activity (Hoffman, A. D. et al., *Virology* 147:326–335 (1985)) in suspension cultures of HIV-infected H9 cells. H9 cells were inoculated with a titered cryopreserved viral stock of H9/HTLV-IIIB at a multiplicity of infection of 0.005. Cells were incubated at $5 \times 10^7$/ml with the inoculum at 37° C. for 60 min to allow viral absorption. The cells were then washed to remove unbound virus, and then resuspended in complete RPMI medium. They were plated at $1 \times 10^5$/ml with or without the addition of MAP 30 at various concentrations for the duration of the experiment. MAP 30 was added at concentrations of 10 ug/ml (334 nM) to 0.01 ug/ml (0.334 nM) in serial ten-fold dilutions. In this assay, at the multiplicity of infection used, viral production peaks at day 4. Thus, p24 expression and HIV-associated RT activity were assayed in cell-free supernatants harvested at day 4. The amount of p24 viral antigen produced was measured by RIA as described in (Nara et al., 1987, supra) and expressed in ng/ml. the HIV-RT activity was assayed by the incorporation of labeled dTTP as described by Hoffman et al. (supra) and expressed in terms of cpm x $10^3$/ml.

Cytotoxicity and Cell Viability

Cytotoxicity of MAP 30 was measured by its effects on cellular synthesis of DNA and protein. The same concentrations of MAP 30 as those used in p24 production and HIV-RT assays (0.01, 0.1, 1.0 and 10 ug/ml) were also added to uninfected cells to assess its effects on cellular DNA or protein synthesis and cell viability. The synthesis of these macromolecules was measured by pulse labeling the cells with 1 µCi of [$^3$H] thymidine or [$^3$H] leucine 8 hours prior to harvesting of cells at day 4. The incorporation of labeled precursor into TCA-precipitable products was determined by scintillation counting. Cell viability was determined by trypan blue dye exclusion.

In Vitro Translation Assay

The ability of MAP 30 to inhibit in vitro translation of eukaryotic cells was measured by the incorporation of [$^3$H]-labeled leucine into TCA-insoluble product in a rabbit reticulocyte lysate system (Pelham, R. B. et al., *Eur. J. Biochem.* 67:247–256 (1976)). This system was obtained from DuPont-New England Nuclear. The reaction mixture contained 1 µg of mRNA, 2 mM magnesium acetate 80 mM potassium acetate translation cocktail (2.5 mM spermidine, 34.5 mg/ml creatine phosphate, 26 mg/ml GTP in 250 mM HEPES buffer) and 1 µCi of [$^3$H]leucine.

RESULTS

Inhibition of Syncytium Formation

The effect of MAP 30 on the infectivity of HIV-1 was measured by the quantitative microtiter infectivity assay.

Figure 4:
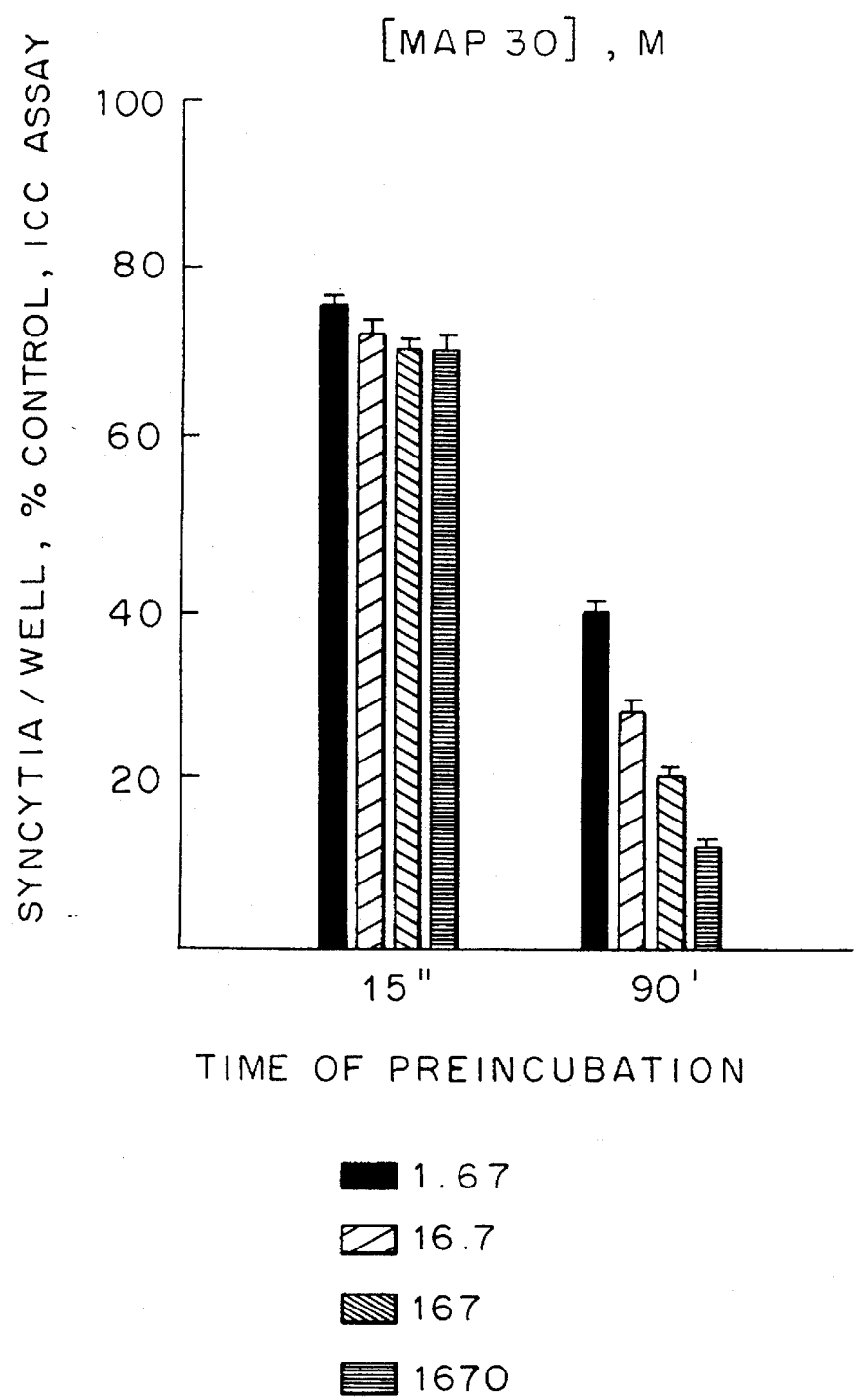
FIG. 4 is a graph showing the effect of MAP 30 on HIV infectivity as assessed by syncytium forming unit (SFU) in the infectious cell center (ICC) assay. The results of syncytium per well are expressed in terms of % control. Experimental conditions were described in the legend of Table 1. Experimental errors are indicated by error bars.

This assay quantitates acute cell free HIV-1 infection and is based on the interaction between fusigenic virus-infected cells expressing the HIV envelope gene paaroducts and unifected adjacent cells bearing CD4 molecules. Focal syncytium formation representing a single infectious virion unit was scored at day 5 (120 hours) by examination under an inverted microscope. The results of two independent experiments are summarized in Table 1 and FIG. 4. A 90 minute preincubation of the indicator cells with MAP 30 resulted in dose-dependent inhibition of HIV infection and replication. At 1.67 nM and 1670 nM, MAP 30 caused 60% and 86% inhibition on syncytium formation respectively. An $ID_{50}$ of 0.83 nM was obtained from these results. At the same concentrations, a 15 sec pre-treatment caused 23% and 25% of specific inhibition, respectively. Under none of these conditions was any cytotoxic or cytostatic effect to the indicator cells observed. Continued presence of MAP 30 in the HIV infected cell culture for 120 hours produced a higher inhibitory effect at all of the concentrations tested, with 61% and 79% inhibition at 1.67 nM and 16.7 nM, respectively. Complete elimination of syncytium formation was observed at 167 nM. These results suggest that MAP 30 affects initial HIV infection as well as transmission of viral gene products through cell contact or release of free virions.

TABLE 1

THE EFFECT OF MAP 30 ON HIV INFECTION AS MEASURED BY SYNCYTIUM FORMATION IN INFECTIOUS CELL CENTER ASSAY OF HIV-INFECTED CEM-SS CELLS

| MAP 30 | | Syncytia/well in ICC Preincubation | | % ICC (Vn/Vo) Preincubation | | Cytotoxicity Preincubation | |
|---|---|---|---|---|---|---|---|
| nM | (μg/ml) | 15" | 90' | 15" | 90' | 15" | 90' |
| 0 (*) | | 94 | 94 | 100 | 100 | — | — |
| 1.67 | (0.05) | 71, 74 | 35, 41 | 77 | 40 | — | — |
| 16.7 | (0.5) | 63, 75 | 31, 23 | 73 | 29 | — | — |
| 167 | (5.0) | 70, 74 | 18, 21 | 71 | 21 | — | — |
| 1670 | (50) | 62, 71 | 16, 10 | 71 | 14 | — | — |

The results are expressed as SFU (syncytium-forming units) per well in terms of percent control. Each test point was carried out in duplicate. Duplicate wells of indicator cells containing MAP 30 at each concentration without virus exposure were included for the determination of MAP 30 cytotoxicity. % ICC (infectious cell center) are expressed in terms of Vn/Vo (average number of syncytia in MAP 30 treated samples/average number of syncytia in untreated controls); the values are the averages of two independent experiments. In the untreated control group (*), the number of syncytia/well is the average of 101, 92, 96, and 87.

Inhibition of Viral Core Protein p24 Expression

Figure 5:
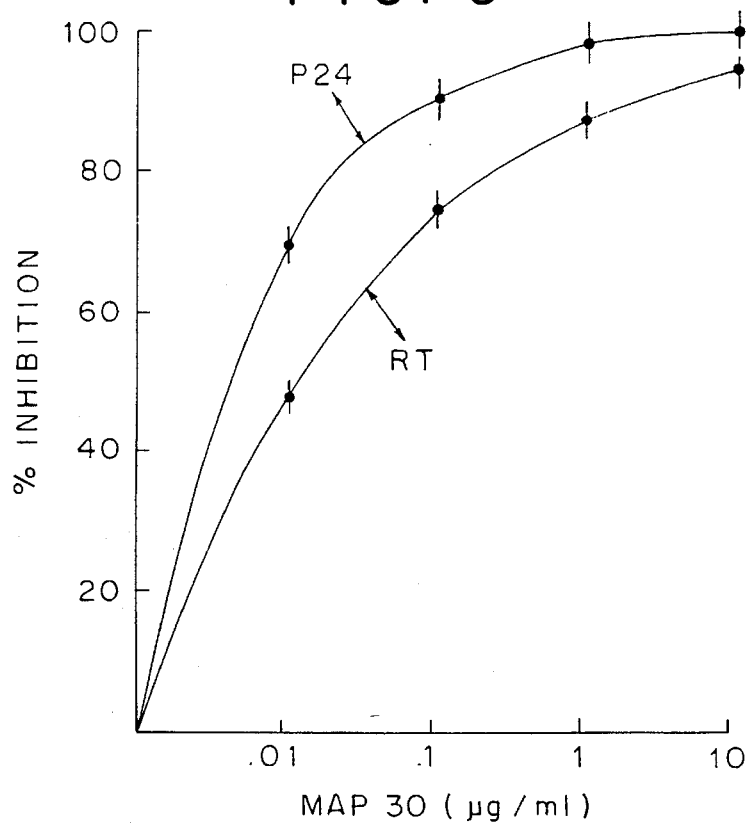
FIG. 5 is a graph showing the effect of MAP 30 on HIV replication as assessed by the production of viral core protein p24 and viral-RT activity. % inhibition is plotted as a function of MAP 30 concentration. Uncertainties are indicated by error bars. Experimental conditions were described in the legend of Table 2.

To assess the antiviral activity of MAP 30 on another human T cell line in suspension culture, viral core protein p24 expression and virus-associated RT activity were examined in HIV-infected H9 cells. The expression of p24 was determined using RIA. The results are shown in Table 2. In the presence of 0.334 nM MAP 30, the expression of p24 was reduced to 29% of the untreated control. As the concentration of MAP 30 was increasd in the culture, inhibition of p24 expression also increased. Virtually complete inhibition was observed at 33.4 nM (1 μg/ml). These results were also expressed in terms of percent inhibition of p24 production as a function of MAP 30 concentration as shown in FIG. 5. The $ID_{50}$ for p24 production was about 0.22 nM. The reduced production of p24 was not due to cytotoxic or cytostatic effects, and no decrease in cellular DNA or protein synthesis was observed at these MAP 30 concentrations.

Inhibition of Viral Associated RT Activity

RT activity was measured using poly (rA).p(dT)$_{12-18}$ as template-primer and [$^3$H] labeled dTTP as substrate. The results are expressed as the polynucleotide incorporation of [$^3$H] label in cpm/ml. As seen in Table 2, HIV-RT activity was reduced to 52, 25, 13, and 6% of control activity, in cells treated with 0.334, 3.34, 33.4, and 334 nM of MAP 30, respectively. These data are also shown in FIG. 5 in terms of % inhibition of RT activity as a function of MAP 30 concentration. The $ID_{50}$ for the activity is likely to be due to a decrease in virion production, which is also evidenced by decreased p24 expression.

TABLE 2

EFFECT OF MAP 30 ON HIV REPLICATION: p24 EXPRESSION AND RT ACTIVITY

| MAP 30 (nM) | p24 Expression | | RT Activity cpm×10$^3$/ml | | % Cell Viab | [$^3$H] Incorp | |
|---|---|---|---|---|---|---|---|
| | ng/ml | % C | | % C | | Thym | Leu |
| 0 | 2106 | 100 | 806 | 100 | 100 | 100 | 100 |
| 0.334 | 610 | 29 | 422 | 52 | 102 | 102 | 101 |
| 3.34 | 189 | 9 | 202 | 25 | 104 | 99 | 102 |
| 33.4 | 42 | 2 | 108 | 13 | 96 | 101 | 98 |
| 334 | 0 | 0 | 52 | 6 | 89 | 75 | 72 | p24 expression and viral-RT activity was assessed in HIV-infected H9 cells. MAP concentrations correspond to 0.01, 0.1, 1, and 10 μg/ml. p24 and RT were measured in culture supernatants harvested on day 4. The values shown are means of duplicate experiments. % C (% of control) is expressed relative to untreated infected controls. p24 is expressed as ng/ml and HIV-RT activity is expressed as cpm × 10$^3$/ml. Cell viability was assessed using trypan blue dye exclusion. Isotope incorporation indicates $^3$H-thymidine or 3H-leucine.

The amount of p24 viral antigen produced was measured by RIA and expressed in ng/ml. Viral associated-RT activity was assayed by the incorporation of [$^3$H]thymidine into acid-insoluble products, using poly(rA)-p(dT)$_{12-18}$ (Pharmacia) as template primer. RT activity was expressed in terms of cpm×10$^3$/ml. The effect on cellular DNA or protein synthesis was measured by pulse labeling the cells with 1 μCi (1 Ci=37 GBq) [$^3$H]thymidine or [$^3$H]leucine 8 hours prior to harvesting. The incorporation of labeled precursor into TCA-precipitable products was determined by scintillation counting. Results are normalized to counts obtained for control cultures without MAP 30. Control cpm: [$^3$H]-thymidine—206,217; [$^3$H]leucine—62,439. Cell viability was determined by trypan blue dye exclusion. Values shown are the averages of duplicates in two independent experiments. Errors are within 6%, as indicated by error bars in FIG. 5.

Inhibition of In Vitro Translation of Eukaryotic Cells

Figure 6:
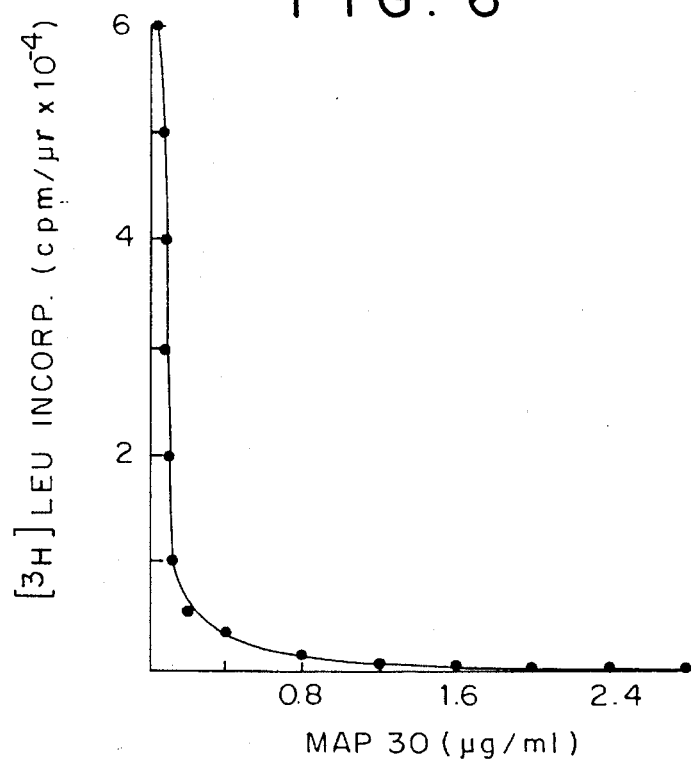
FIG. 6 is a graph showing the effect of MAP 30 on eukaryotic translation. The ribosome inactivating activity of MAP 30 was studies using reticulocyte lysate translation kit (DuPont/New England Nuclear). Protein biosynthesis was measured by the incorporation of [$^3$H] leucine into acid insoluble product. The inhibitory effect of MAP 30 was expressed in terms of incorporation of [$^3$H] leucine (cpmx$10^4$/μl) as a function of MAP 30 concentration.

In view of the sequence homology between MAP 30 and these ribosome inactivating proteins, the effect of MAP 30 on in vitro eukaryotic translation was assayed in a rabbit reticulocyte lysate system. The results are shown in FIG. 6. The effect of MAP 30 on protein biosynthesis is expressed as the incorporation of [$^3$H] labeled leucine into TCA insoluble product. MAP 30 exhibited a dose-dependent inhibition of cell-free translation with an $ID_{50}$ of 3.3 nM.

EXAMPLE III

MAP 30 IS NOT TOXIC TO INTACT CELLS

Assays of Cytotoxicity

In order to ascertain that the anti-HIV activity of MAP 30 is virus specific, the effect of MAP 30 on cellular DNA or protein synthesis was determined in unifected H9 cells. The incorporations of [$^3$H]thymidine or [$^3$H]leucine into trichloroacetic acid (TCA)-precipitable DNA or protein were measured by pulse labeling experiments. These reults are shown in Table 2. From 0.334 to 33.4 nM, MAP 30 caused no detectable effect on cellular incorporation of labeled thymidine or leucine, while the majority of p24 and HIV-RT productions were inhibited. Even at 334 nM (in the range of 1000 times the $ID_{50}$), MAP 30 only yielded 25% reductions in cellular DNA or protein synthesis respectively, as compared to virtually total inhibition of p24 and HIV-RT production in HIV-infected H9 cells. A therapeutic index of at least 1,000 was observed.

EXAMPLE IV

ANTITUMOR ACTIVITY OF MAP 30

MAP 30 is added to tumor cells in vitro or is used to treat animals having tumors in vivo. The protein has preferential cytotoxicity for human leukemia cells, being at least 10 times more potent in killing leukemia cells compared to normal human peripheral blood lymphocytes. MAP 30 also shows in vivo antitumor activity in mice. For example, pretreatment of tumor cells (such as P388 or L1210) with MAP 30 prior to their intraperitoneal implantation, followed by biweekly intraperitoneal injection of MAP 30 (at doses between about 1 to 100 µg) produces a significant antitumor effect and prolongs survival of the treated animals. The concentrations used for treatment in vivo are not toxic to the mice over the period of treatment.

EXAMPLE V

N-TERMINAL AMINO ACID SEQUENCE OF MAP 30

Sequence Analysis

The N-terminal amino acid sequence of MAP 30 was determined by automated Edman degradation using an Applied Biosystems model 470A protein sequencer, with on-line PTH analyzer.
N-Terminal Sequence of MAP 30

The sequence of the first 44 amino acids from the N-terminus is shown in FIG. 7. This represents the first protein sequence data from the plant Momordica charantia. A search in the EMBL protein databank and a structural analysis of MAP 30 sequence reveal homology with the N-terminal amino acid sequences of ricin A chan and trichosanthin. The EMBL data bank reveals 34% homology to ricin A chain and 57% homology to trichosanthin when both identical and conserved residues are considered. When only identical residues are considered, the homology is reduced to 25% and 43% respectively. Like ricin and trichosanthin, MAP 30 also inhibits in vitro translation of eukaryotic cells. Distinct from these compounds, MAP 30 is not toxic to intact normal cells.

Ricin is a plant toxin, composed of two 25 kDa subunits (a and B chains) linked by a disulfide bridge. The B chain of the toxin binds to the surface of eukaryotic cells and enables the entrance of the A chain. the A chain is the catalytic subunit of the molecule, which upon internatlization inhibits protein synthesis in the cell. MAP 30 is clearly different from ricin in that it is a single chain polypeptide, and it is not toxic to intact cells.

Trichosanthin is a 26 kDa plant protein isolated from the root tuber of Trichosanthes. This protein has been used for inducing abortions and for treating trophoblastic tumors (Qian, R. Q. et al., *Acta Chem. Sinica* 39:927–31 (1981); Gu., Z. et al., *Acta Chem. Sinica* 43:943–945 (1984); Lan, I. F., et al., *Contraception* 21:77–86 (1980); Cheng, K. F., Obstet. Gynecol. 59: 494–498 (1982); Chan, W. Y. et al., *Contraception* 29:91–100 (1984)). It has also been shown to inhibit protein synthesis in vitro (Maraganore, J. M. et al., *J. Biol. Chem.* 262:11628–11633 (1987)). Recently, trichosanthin, referred to as GLQ 223, was reported to have anti-HIV activity (McGrath, M. S. et al., supra). It is important to note that under identical assay conditions, MAP 30 is much less cytotoxic as compared to GLQ 223. For example, at $ID_{90}$ (inhibitory dose at 90% inhibition) for HIV-RT activity, GLQ 223 caused about 35% and 40% inhibition on cellular synthesis of DNA and protein respectively whereas at the same inhibitory dose, MAP 30 showed no detectable inhibition on the synthesis of these macromolecules (Table 2). Even at 10 times its $ID_{90}$, MAP 30 caused only 25% and 28% inhibition on cellular incorporation of [$^3$H]thymidine and leucine respectively. MAP 30 is thus at least one order of magnitude lower in cytotoxicity than GLQ223. The associated toxic effects of GLQ223 have been well documented and have raised serious concerns regarding its clinical utility. The low in vitro cytotoxicity of MAP 30 indicates that it may have a much better therapeutic index.

The isolation of several other bioactive proteins from Momordica charantia has been reported, some of which have ribosome inactivating activity and others which can inhibit tumor development in animals or viral replication in culture. These proteins have been termed *Momordica charantia* inhibitors (MCI), having molecular weights of 23–24 kDa, and momorcharin alpha and beta (MCA and MCB) and have molecular weights of 32 and 28 kDa, respectively. No amino acid sequence data is available on these proteins which would permit comparison with the sequence of MAP 30.

EXAMPLE VI

MOLECULAR CLONING OF MAP 30

Poly A+ mRNA was prepared from Momordica charantia as described above. A cDNA library was constructed in lambda gt11 as described above. The library was screened by plaque hybrdization using oligonucleotide probes derived from the N-terminal amino acid sequence of MAP 30. These oligonucleotides were described earlier. Several positive clones have been identified.

The clones are sequenced according to standard methods (see above) to determine the nucleotide sequence of the MAP 30 gene, and, from this, the amino acid sequence of the MAP 30 protein.

The cloned gene is expressed in bacterial and eukaryotic cells according to methods described above.

EXAMPLE VII

CONJUGATION OF MAP 30 TO ANTI-HIV ANTIBODIES

MAP 30 is cross-linked to human anti-gp41 and human anti-gp120 monoclonal antibodies using the heterobifucntional reagent, SPDP (N-succinimidyl 3-(2-pyridyldithio)propionate. Purified antibody in phosphate buffered saline is treated with SPDP in 10–15 -fold molar excess for 30 min. at room temperature so as to introduce 2-pyridyl disulfide groups into the IgG molecule. The free SPDP is removed by dialysis. The sample is then mixed with MAP 30 (3-fold molar excess) at 4° C. for 16 hours. The conjugate is separated from unbound MAP 30 by gel filtration on a Sephacryl S-200 column.

The cytotoxic effect of the conjugate is tested on CEM, H9 and U1 cells, as described above. The conjugate is shown to have specific cytotoxic activity for HIV infected, but not for uninfected target cells.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

---

What is claimed is:

1. A purified protein comprising a MAP 30 protein obtainable from the fruit or the seed of the plant *Momordica charantia*, said MAP 30 protein having a molecular weight of about 30 kD on sodium dodecyl sulfate polyacrylamide gel electrophoresis and including the amino acia sequence: Asp-Val-Asn-Phe-Asp-Leu-Ser-Thr-Ala-Thr-Ala-Lys-Thr-Tyr-Thr-Lys -Phe-Ile-Glu-Asp-Phe-Arg-Ala-Thr-Leu-Pro-Phe-Ser-His-Lys-Val -Tyr-Asp-Ile-Pro-Leu-Leu-Tyr-Ser-Thr-Ile-Ser-Asp-Pro, SEQ ID NO:1, said protein having anti-HIV activity in vitro in p24 expression or reverse transcriptase assays.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Asp Val Asn Phe Asp Leu Ser Thr Ala Thr Ala Lys Thr Tyr Thr Lys
1               5                   10                  15
Phe Ile Glu Asp Phe Arg Ala Thr Leu Pro Phe Ser His Lys Val Tyr
            20                  25                  30
Asp Ile Pro Leu Leu Tyr Ser Thr Ile Ser Asp Pro
            35                  40          44
```

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:2:

GAY GTN AAY TTY GAY CT                    17

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GGTGGCGACG ACTCCTGGAG CCCG                24

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

TTGACACCAG ACCAACTGGT AATG  24